United States Patent
Field et al.

(10) Patent No.: US 10,241,013 B2
(45) Date of Patent: Mar. 26, 2019

(54) INLINE DILUTION AND AUTOCALIBRATION FOR ICP-MS SPECIATION ANALYSIS

(71) Applicant: Elemental Scientific, Inc., Omaha, NE (US)

(72) Inventors: Paul Field, Papillion, NE (US); Daniel R. Wiederin, Omaha, NE (US); Patrick Sullivan, Omaha, NE (US)

(73) Assignee: ELEMENTAL SCIENTIFIC, INC., Omaha, NE (US)

(*) Notice: Subject to any disclaimer, the term of this patent is extended or adjusted under 35 U.S.C. 154(b) by 133 days.

(21) Appl. No.: 15/368,803

(22) Filed: Dec. 5, 2016

(65) Prior Publication Data

US 2017/0162373 A1 Jun. 8, 2017

Related U.S. Application Data

(60) Provisional application No. 62/264,661, filed on Dec. 8, 2015.

(51) Int. Cl.
| | |
|---|---|
| *G01N 1/38* | (2006.01) |
| *G01N 30/04* | (2006.01) |
| *G01N 35/10* | (2006.01) |
| *G01N 30/00* | (2006.01) |
| *H01J 49/10* | (2006.01) |

(52) U.S. Cl.
CPC ............... *G01N 1/38* (2013.01); *G01N 30/00* (2013.01); *G01N 30/04* (2013.01); *G01N 35/1097* (2013.01); *G01N 2035/1032* (2013.01); *H01J 49/105* (2013.01)

(58) Field of Classification Search
CPC ...... G01N 1/38; G01N 30/24; G01N 35/1097; G01N 2035/1032
See application file for complete search history.

(56) References Cited

U.S. PATENT DOCUMENTS

| | | | | |
|---|---|---|---|---|
| 5,308,774 | A * | 5/1994 | Miura .................... | G01N 35/00 436/111 |
| 7,229,841 | B2 * | 6/2007 | Tamarkin ............. | A61K 38/191 436/518 |
| 7,384,604 | B2 * | 6/2008 | Eaton ...................... | G01N 1/38 422/417 |
| 7,507,336 | B2 * | 3/2009 | Quimby .................. | B01L 3/565 210/198.2 |

(Continued)

*Primary Examiner* — Justin N Olamit
(74) *Attorney, Agent, or Firm* — Kevin E. West; Advent, LLP

(57) ABSTRACT

Systems and methods for inline and automatic dilution of chemicals of interest for speciation and subsequent analysis by ICP spectrometry are described. A system embodiment includes a first valve to receive a sample into a holding loop; a plurality of syringe pumps coupled to the first valve to deliver an inline diluted sample from the first valve; and a second valve coupled to the first valve to receive the inline diluted sample from the first valve into a sample holding loop coupled to the second valve, the second valve configured to couple to at least one of an eluent source or a carrier fluid source to receive at least one of an eluent fluid or a carrier fluid to transfer the inline diluted sample from the sample holding loop to a speciation column to separate one or more species from the inline diluted sample.

10 Claims, 11 Drawing Sheets

(56) References Cited

U.S. PATENT DOCUMENTS

| | | | | |
|---|---|---|---|---|
| 8,118,050 B1* | 2/2012 | Wiederin | ................. | G01N 1/38 |
| | | | | 137/111 |
| 9,717,841 B2* | 8/2017 | McNeil | ............... | A61M 1/3486 |
| 2010/0050737 A1* | 3/2010 | Wolters | ............. | G01N 30/8665 |
| | | | | 73/23.22 |
| 2011/0016955 A1* | 1/2011 | Cormier | ................... | G01N 1/38 |
| | | | | 73/61.55 |

\* cited by examiner

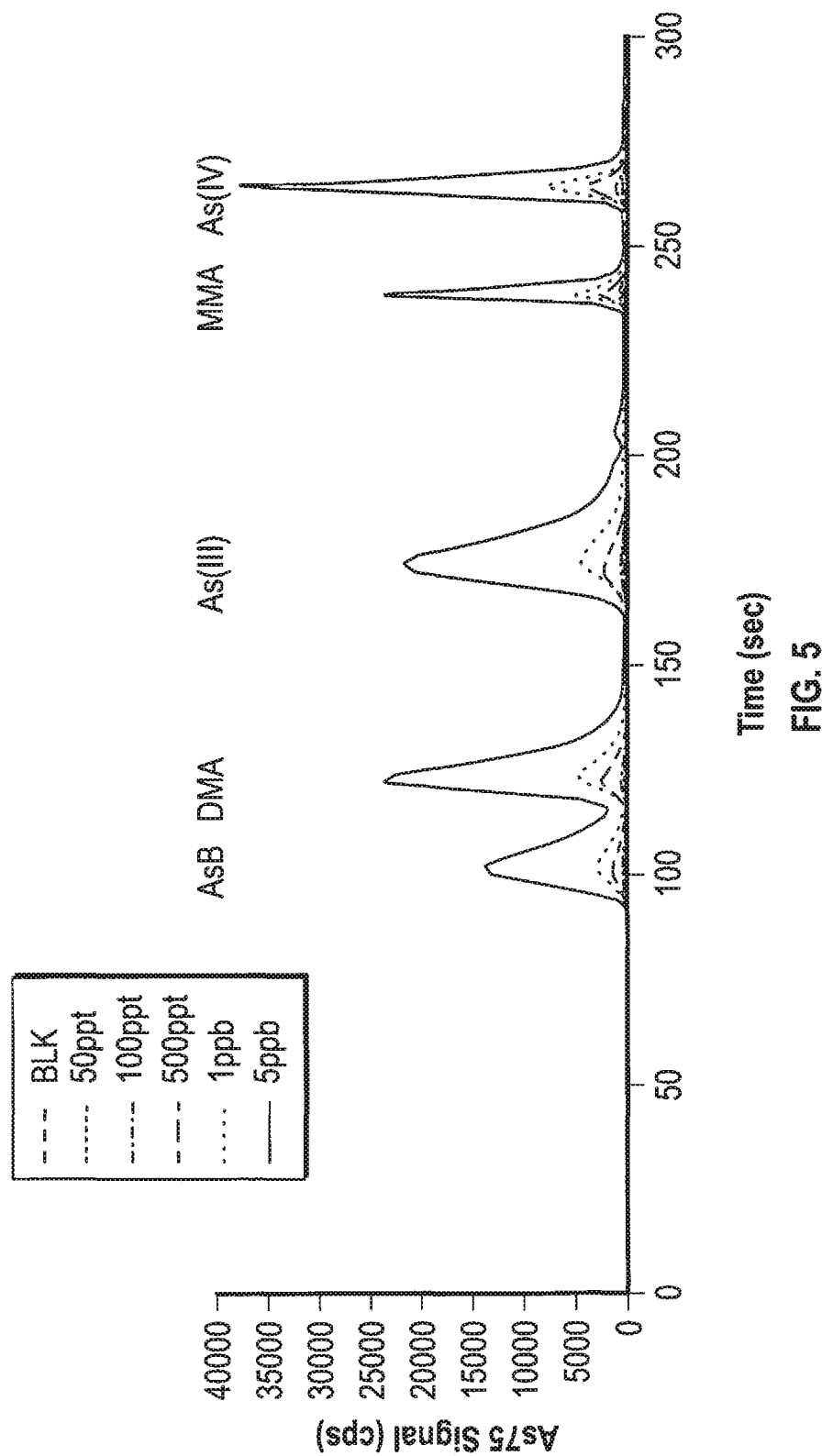

INLINE DILUTION AND AUTOCALIBRATION FOR ICP-MS SPECIATION ANALYSIS

CROSS-REFERENCE TO RELATED APPLICATIONS

The present application claims the benefit under 35 U.S.C. § 119(e) of U.S. Provisional Application Ser. No. 62/264,661, filed Dec. 8, 2015, and titled "INLINE DILUTION AND AUTOCALIBRATION FOR ICP-MS SPECIATION ANALYSIS." U.S. Provisional Application Ser. No. 62/264,661 is herein incorporated by reference in its entirety.

BACKGROUND

Spectrometry refers to the measurement of radiation intensity as a function of wavelength to identify component parts of materials. Inductively Coupled Plasma (ICP) spectrometry is an analysis technique commonly used for the determination of trace element concentrations and isotope ratios in liquid samples. For example, in the semiconductor industry, ICP spectrometry can be used to determine metal concentrations in samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample. The sample to be analyzed is often provided in a sample mixture.

Sample introduction systems may be employed to introduce liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods for inline and automatic dilution of chemicals of interest for speciation and subsequent analysis by ICP spectrometry are described. A system embodiment includes a first valve to receive a sample into a holding loop; a plurality of syringe pumps coupled to the first valve to deliver an inline diluted sample from the first valve; and a second valve coupled to the first valve to receive the inline diluted sample from the first valve into a sample holding loop coupled to the second valve, the second valve configured to couple to at least one of an eluent source or a carrier fluid source to receive at least one of an eluent fluid or a carrier fluid to transfer the inline diluted sample from the sample holding loop to a speciation column to separate one or more species from the inline diluted sample.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. In the figures, the use of the same reference numbers in different instances in the description and the figures may indicate similar or identical items.

FIG. 5 is a calibration chromatogram overlay via autocalibration of a single mixed standard and a calibration blank.

DETAILED DESCRIPTION

Figure 1:
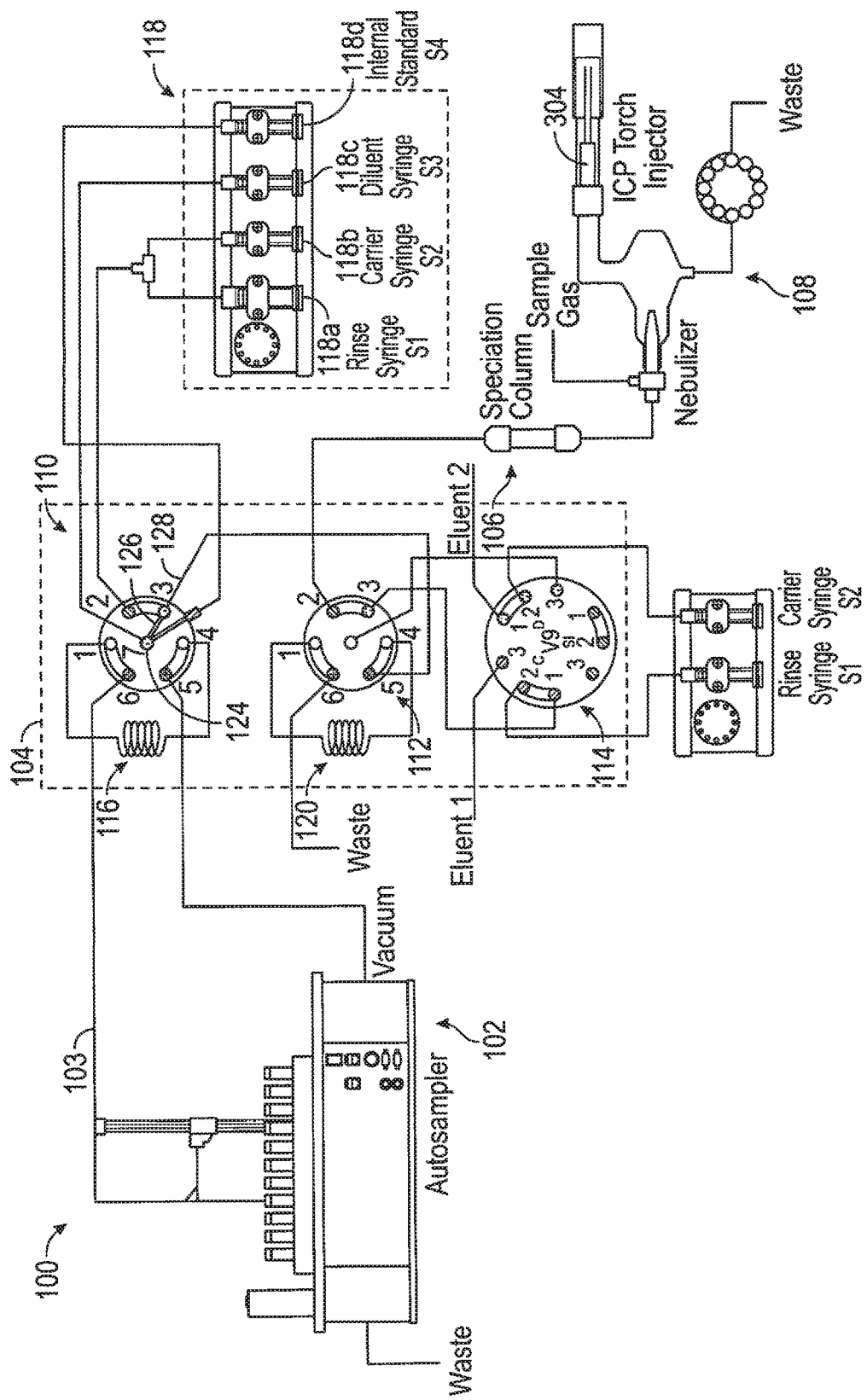
FIG. 1 is an illustration of an ICP spectrometry system for inline dilution of samples for speciation analysis in accordance with example implementations of the present disclosure.

Referring to FIGS. 1-9, systems and methods for inline and automatic dilution of chemicals of interest for speciation and subsequent analysis by ICP-MS are described. Analysis of the various species of an element is an important aspect of sample analysis, particularly where an assay of the particular element alone may not provide all relevant information associated with that element. For instance, differing species of an element can have remarkably different toxicity levels, where knowledge of an amount of the element in general does not provide an indication as to the toxicity of that element. For example, one species of chromium (e.g., Cr(III)) can provide nutritive benefits, whereas another species of chromium (e.g., Cr(VI)) is toxic to humans as a carcinogen. As another example, some organic arsenic species (e.g., arsenobetaine (AsB)) can be relatively non-toxic or have low toxicity, whereas inorganic arsenic species (e.g., arsenite (As(III)), arsenate (As(V))) are highly toxic.

ICP-MS can be utilized to determine the presence of certain chemical elements, even at extremely low concentrations, however ICP-MS does not typically distinguish between differing species of the chemical elements. One procedure to differentiate different species of an element includes using a separation column (e.g., a speciation column) to separate the differing species from a fluid stream over time, where the species can be measured at the ICP-MS as peaks of the element at various times as the species are separated. The peaks can be influenced by the matrix compositions of the various materials sampled, which can include food materials (e.g., apple juice, rice flour, etc.). For example, the shape of the peak, the times at which the peaks arise, etc., can be influenced by the matrix compositions of the sample. To avoid large deviations in the sample analysis, the samples can be diluted to lower concentrations to minimize the effects of the matrix on the sample analysis, such as by avoiding substantial changes to the chemistry of the particular speciation column. However, attempting to pre-dilute the sample can cause species of the particular element of interest to convert to a different species of that element, resulting in an erroneous analysis of the amount of species by the ICP-MS. For example, it has been determined that organic species of arsenic (e.g., arsenobetaine (AsB), dimethylarsinic acid (DMA), and monomethylarsonic acid (MMA)) can covert to inorganic species of arsenic (e.g., arsenate (As(V))) when manually pre-diluted in a sample vial (e.g., a sample vial accessible by an autosampler). Thus, while the total amount of the chemical element of interest would be measured the same by the ICP-MS, the amount of the individual species of the chemical element of interest would differ due to the conversion of one species of the chemical element to another species prior to analysis. Further, while high pressure liquid chromatography (HPLC) can be utilized for speciation, such HPLC systems typically include metal components or parts to facilitate the required high pressures of the systems, which can pose a contamination risk for detecting low concentrations of chemical elements.

Accordingly, the present disclosure is directed to systems and methods for inline and automatic dilution of chemicals of interest for speciation and subsequent analysis by ICP-MS. By providing inline and automatic dilution, chemicals can be speciated and analyzed in real time, rather than pre-diluting each sample (e.g., in a sample vial) and allowing the samples to wait for an autosampler to remove the pre-diluted sample for speciation and analysis (which can provide time for the species to convert to a different species of the chemical of interest). While specific examples are provided herein directed to arsenic and arsenic species, the systems and methods for automatic inline dilution are not limited to arsenic and arsenic species and can encompass any and all solutions that may not be stable in a diluted form for any period of time after preparation. Examples include not only other elements, but also immiscible or partially miscible solutions, such as oils, etc. The systems described herein can operate at low pressures via syringe pumps (e.g., as opposed to peristaltic pumps) in a clean system to provide chemical assays with high accuracy. For example, in an implementation, the systems described herein include no metallic component in contact with the sample fluid, which can prevent a risk of metallic contamination associated with such contact.

In the following discussion, example implementations of techniques for providing inline and automatic dilution of chemicals of interest for speciation and subsequent analysis by ICP-MS are presented.

EXAMPLE IMPLEMENTATIONS

FIG. 1 illustrates a system 100 for providing inline and automatic dilution of chemicals of interest for speciation and subsequent analysis by ICP-MS in an example implementation. As shown, the system 100 generally includes a sampling device 102 (e.g., autosampler), a valve system 104, and a speciation column 106 in fluid communication with an ICP torch assembly 108. The valve system 104 includes one or more valves switchable between a plurality of positions to facilitate flow of various fluids (e.g., sample fluids, carrier fluids, diluent fluids, internal standard fluids, eluent fluids, rinse fluids, etc.) through the system 100. In an implementation, the valve system 104 includes at least a first valve 110, a second valve 112, and a third valve 114. For example, one or more of the first valve 110, the second valve 112, and the third valve 114 can be rotary valves switchable between valve configurations to facilitate different flow paths for fluids flowing through the respective valve between different valve configurations. The first valve 110 is coupled to the sampling device 102 to receive a sample 103 and to hold the received sample 103, such as in a holding loop 116. For example, in an implementation the first valve 110 is switchable between at least two configurations, wherein in a first valve configuration, the first valve 110 provides a flow path to receive the sample 103 from the sampling device 102 and direct the received sample 103 to the holding loop 116. The first valve 110 is also coupled to a pump system 118 configured to supply to the first valve 110 one or more internal standards, diluents, carriers, and rinse solutions. In an implementation, the pump system 118 includes a plurality of syringe pumps shown as 118a, 118b, 118c, and 118d that are controlled to move each respective syringe at a particular rate to create desired dilutions of the sample and/or standard additions to the sample at the first valve 110. For example, the first valve 110 can switch to a second valve configuration having a flow path to receive a carrier fluid from the carrier syringe pump 118b, a diluent fluid from the diluent syringe pump 118c, and a standard fluid from the standard syringe pump 118d, whereby the fluids provide inline dilution of the sample 103 and deliver the diluted sample from the first valve 110 to the second valve 112. While four syringe pumps are shown in FIG. 1, it is can be appreciated that fewer than four syringe pumps or greater than four syringe pumps could also be utilized. In an implementation, each of the syringe pumps of the pump system 118 (e.g., syringe pumps 118a, 118b, 118c, and 118d) can operate at a particular injection rate to provide the controlled dilution or the controlled standard addition at the first valve 110. As an example, the following table 1 illustrates flow rates for standard (e.g., via syringe pump 118d) and diluent (e.g., via syringe pump 118c) to provide various inline dilution factors (e.g., from the first valve 110) for automatic preparation of various calibration curves. In an implementation the diluent, standard, and/or sample can be mixed via a mixing portion of the first valve 110, where the mixing portion can include one or more of a mixing port 124, a mixing channel 126, and a fluid transfer line 128 coupled between the first valve 110 and the second valve 112, to bring the diluent, standard, and/or sample together for mixing. The inline dilution factors can be prepared for individual species of an element (e.g., Cr(III) and Cr(VI); arsenobetaine (AsB), dimethylarsinic acid (DMA), monomethylarsonic acid (MMA) arsenite (As(III)), and arsenate (As(V)); etc.), such as to provide individualized calibration curves for each species under analysis.

TABLE 1

Calibration Curve Flow Rates

| Standard Position | Inline Dilution Factor | Standard Flow Rate (µL/min) | Diluent Flow Rate (µL/min) | Total Flow Rate (µL/min) | Concentration (100 ppt) |
|---|---|---|---|---|---|
| 1 (Blank) | 200x | 50 | 9950 | 10000 | 0 |
| 2 (Species A) | 20x | 500 | 9500 | 10000 | 5 |
| 2 (Species A) | 10x | 1000 | 9000 | 10000 | 10 |
| 2 (Species A) | 6.6x | 1500 | 8500 | 10000 | 15 |
| 2 (Species A) | 5x | 2000 | 8000 | 10000 | 20 |
| 2 (Species A) | 4x | 2500 | 7500 | 10000 | 25 |
| 2 (Species A) | 2x | 5000 | 5000 | 10000 | 50 |

Figure 2:
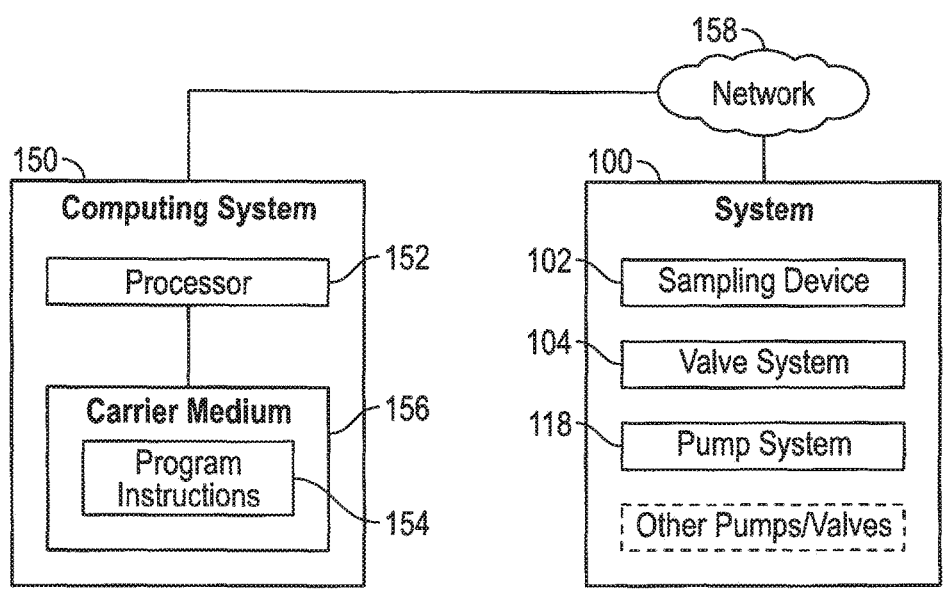
FIG. 2 is a block diagram illustrating a computing system for controlling a system for inline dilution of samples for speciation analysis by an ICP spectrometry system, such as the system shown in FIG. 1.
Figure 3A:
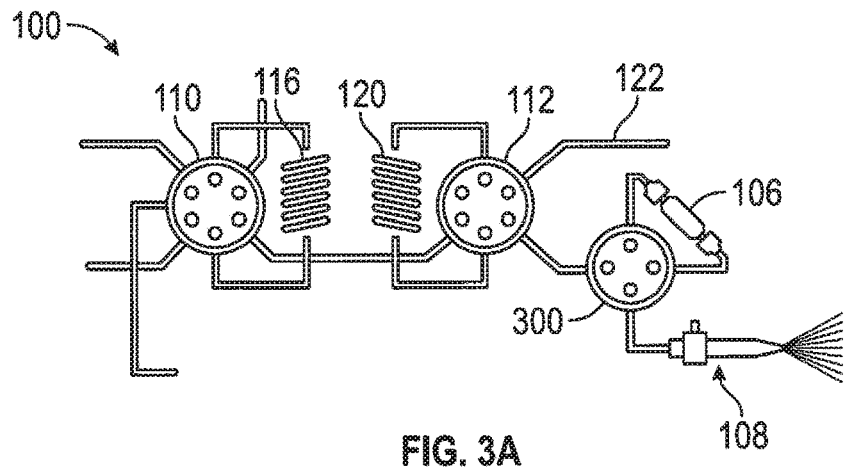
FIGS. 3A through 3C are schematic illustrations of a valve system including a speciation bypass valve for a system for inline dilution of samples for speciation analysis by an ICP spectrometry system.
Figure 3B:
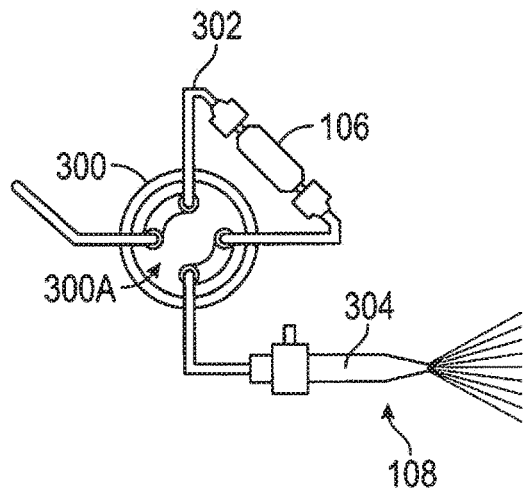
Figure 3C:
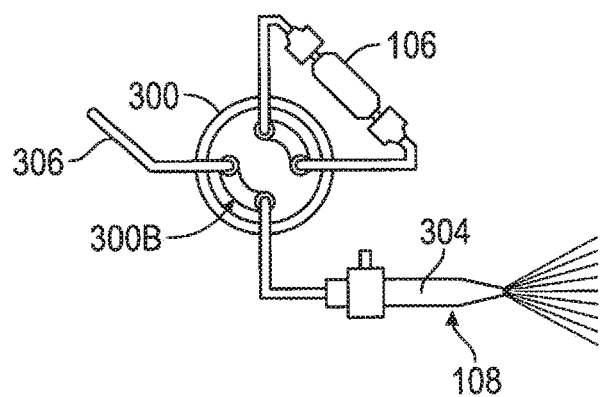

In an implementation, the inline dilution factors are facilitated through automatic control of one or more components of the system 100. For example, electromechanical devices (e.g., electrical motors, servos, actuators, or the like) may be coupled with or embedded within the valve system 104 (e.g., the first valve 110, the second valve 112, the third valve 114, etc.), and/or the pump system 118 (e.g., syringe pumps 118a, 118b, 118c, and 118d, etc.), and/or another pump/valve to facilitate automated operation via control logic embedded within or externally driving the system 100. The electromechanical devices can be configured to cause the plurality of valves to direct fluid flows from syringe pumps 118a, 118b, 118c, and 118d, and from other syringes, flow paths, eluent sources, etc., according to one or more modes of operation. As shown in FIG. 2, the auto-sampling system 100 may be controlled by a computing system 150 having a processor 152 configured to execute computer readable program instructions 154 (i.e., the control logic) from a non-transitory carrier medium 156 (e.g., storage medium such as a flash drive, hard disk drive, solid-state disk drive, SD card, optical disk, or the like). The computing system 150 can be connected to various components of the system 100, either by direct connection, or through one or more network connections 158 (e.g., local area networking (LAN), wireless area networking (WAN or WLAN), one or more hub connections (e.g., USB hubs), and so forth). For example, the computing system 150 can be communicatively coupled to the sampling device 102, the valve system 104, the pump system 118, components thereof, any of the various pumps or valves provided herein, or combinations thereof. The program instructions 154, when executing by processor 152, can cause the computing system 150 to control the auto-sampling system 100 (e.g., control the pumps and valves) according to one or more modes of operation (e.g., automatic calibration curve(s), sample collection, sample dilution, speciation, speciation bypass, etc.), as described herein. In an implementation, the program instructions 154 form at least a portion of software programs for execution by the processor 152.

The processor 152 provides processing functionality for the computing system 150 and may include any number of processors, micro-controllers, or other processing systems, and resident or external memory for storing data and other information accessed or generated by the computing system 150. The processor 152 is not limited by the materials from which it is formed or the processing mechanisms employed therein and, as such, may be implemented via semiconductor(s) and/or transistors (e.g., electronic integrated circuits (ICs)), and so forth.

The non-transitory carrier medium 156 is an example of device-readable storage media that provides storage functionality to store various data associated with the operation of the computing system 150, such as a software program, code segments, or program instructions 154, or other data to instruct the processor 152 and other elements of the computing system 150 to perform the techniques described herein. Although a single carrier medium 156 is shown in FIG. 2, a wide variety of types and combinations of memory may be employed. The carrier medium 156 may be integral with the processor, stand-alone memory, or a combination of both. The carrier medium 156 may include, for example, removable and non-removable memory elements such as RAM, ROM, Flash (e.g., SD Card, mini-SD card, micro-SD Card), magnetic, optical, USB memory devices, and so forth. In embodiments of the computing system 150, the carrier medium 156 may include removable ICC (Integrated Circuit Card) memory such as provided by SIM (Subscriber Identity Module) cards, USIM (Universal Subscriber Identity Module) cards, UICC (Universal Integrated Circuit Cards), and so on.

The computing system 150 can include one or more displays to display information to a user of the computing system 150. In embodiments, the display may comprise a CRT (Cathode Ray Tube) display, an LED (Light Emitting Diode) display, an OLED (Organic LED) display, an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The display may be backlit via a backlight such that it may be viewed in the dark or other low-light environments. The display may be provided with a touch screen to receive input (e.g., data, commands, etc.) from a user. For example, a user may operate the computing system 150 by touching the touch screen and/or by performing gestures on the touch screen. In some embodiments, the touch screen may be a capacitive touch screen, a resistive touch screen, an infrared touch screen, combinations thereof, and the like. The computing system 150 may further include one or more input/output (I/O) devices (e.g., a keypad, buttons, a wireless input device, a thumbwheel input device, a trackstick input device, and so on). The I/O devices may include one or more audio I/O devices, such as a microphone, speakers, and so on.

The computing system 150 may also include a communication module representative of communication functionality to permit computing device to send/receive data between different devices (e.g., components/peripherals) and/or over the one or more networks 158. The communication module may be representative of a variety of communication components and functionality including, but not necessarily limited to: a browser; a transmitter and/or receiver; data ports; software interfaces and drivers; networking interfaces; data processing components; and so forth.

The one or more networks 158 are representative of a variety of different communication pathways and network connections which may be employed, individually or in combinations, to communicate among the components of the inline dilution and autocalibration system environment (e.g., system 100). Thus, the one or more networks 158 may be representative of communication pathways achieved using a single network or multiple networks. Further, the one or more networks 158 are representative of a variety of different types of networks and connections that are contemplated including, but not necessarily limited to: the Internet; an intranet; a Personal Area Network (PAN); a Local Area Network (LAN) (e.g., Ethernet); a Wide Area Network (WAN); a satellite network; a cellular network; a mobile data network; wired and/or wireless connections; and so forth. Examples of wireless networks include, but are not necessarily limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through Universal Serial Bus (USB), Ethernet, serial connections, and so forth.

The computing system 150 is described as including a user interface, which is storable in memory (e.g., the carrier medium 156) and executable by the processor 152. The user interface is representative of functionality to control the display of information and data to the user of the computing system 150 via the display. In some implementations, the display may not be integrated into the computing system 150 and may instead be connected externally using universal serial bus (USB), Ethernet, serial connections, and so forth. The user interface may provide functionality to allow the user to interact with one or more applications of the computing system 150 by providing inputs (e.g., sample identities, desired dilution factors, standard identities, eluent identities/locations, etc.) via the touch screen and/or the I/O devices. For example, the user interface may cause an application programming interface (API) to be generated to expose functionality to an online dilution control module to configure the application for display by the display or in combination with another display. In embodiments, the API may further expose functionality to configure an inline dilution control module to allow the user to interact with an application by providing inputs via the touch screen and/or the I/O devices to provide desired dilution factors for analysis.

The inline dilution control module may comprise software, which is storable in memory (e.g., the carrier medium 156) and executable by the processor 152, to perform a specific operation or group of operations to furnish functionality to the computing system 150. The inline dilution control module provides functionality to control the dilution of, for example, an internal standard and/or the samples from the sampling device 102. For example, the inline dilution control module may control amounts of the carrier and/or the diluent that are supplied by pumps of the pump system 118 (e.g., to the first valve 110 for mixing with the sample 103 carried from the holding loop 116).

In implementations, the user interface may include a browser (e.g., for implementing functionality of the inline dilution control module). The browser enables the computing device to display and interact with content such as a webpage within the World Wide Web, a webpage provided by a web server in a private network, and so forth. The browser may be configured in a variety of ways. For example, the browser may be configured as an inline dilution control module accessed by the user interface. The browser may be a web browser suitable for use by a full resource device with substantial memory and processor resources (e.g., a smart phone, a personal digital assistant (PDA), etc.).

Generally, any of the functions described herein can be implemented using software, firmware, hardware (e.g., fixed logic circuitry), manual processing, or a combination of these implementations. The terms "module" and "functionality" as used herein generally represent software, firmware, hardware, or a combination thereof. The communication between modules in the system 100, for example, can be wired, wireless, or some combination thereof. In the case of a software implementation, for instance, a module may represent executable instructions that perform specified tasks when executed on a processor, such as the processor 152 described herein. The program code can be stored in one or more device-readable storage media, an example of which is the non-transitory carrier medium 156 associated with the computing system 150.

Referring again to FIG. 1, the second valve 112 is shown coupled between the first valve 110 and the third valve 114 and is configured to receive fluids from the first valve 110 and the third valve 114. For example, in an implementation the second valve 112 is switchable between at least two configurations, wherein in a first valve configuration, the second valve 112 provides a flow path to receive the diluted sample from the first valve 110 and direct the diluted sample to a sample holding loop 120. The second valve 112 is also coupled to the speciation column 106, such as to introduce fluids received from the first valve 110 and the third valve 114 to the speciation column 106. For example, the second valve 112 can switch to a second valve configuration to provide a flow path that can introduce one or more of the sample, diluted sample solution, standard solution, diluted standard solution, or the like from the holding loop 120 (or directly from the first valve 110) to the speciation column 106 to separate the various species of the chemical of interest. In an implementation, once the sample or diluted sample has been introduced to the speciation column 106, the second valve 112 can introduce one or more eluents received from the third valve 114 for transferring the species of interest from the speciation column 106 to the ICP torch assembly 108 for ICP-MS analysis.

In an implementation, the system 100 can alternate between speciation analysis of the sample 103 and a total metals analysis of the sample without speciation. For example, referring to FIGS. 3A-3C, the system 100 can include a speciation bypass valve 300 coupled between the second valve 112 and the speciation column 106. The speciation bypass valve 300 is switchable between at least two configurations, with at least a speciation configuration 300A (shown in FIG. 3B) and a speciation bypass configuration 300B (shown in FIG. 3C). In the speciation configuration 300A, fluid received from the second valve 112 (e.g., diluted sample fluid held in the sample holding loop 120, eluent from an eluent source via fluid line 122, etc.) can flow along flow path 302 through the speciation bypass valve 300 and the speciation column 106 to the ICP torch assembly 108 (with an injector 304 shown) for analysis by the ICP instrument. In the speciation bypass configuration 300B, fluid received from the second valve 112 is not received in the speciation column 106 and instead flows along flow path 306 to the ICP torch assembly 108 (with an injector 304 shown) for analysis by the ICP instrument.

Figure 4A:
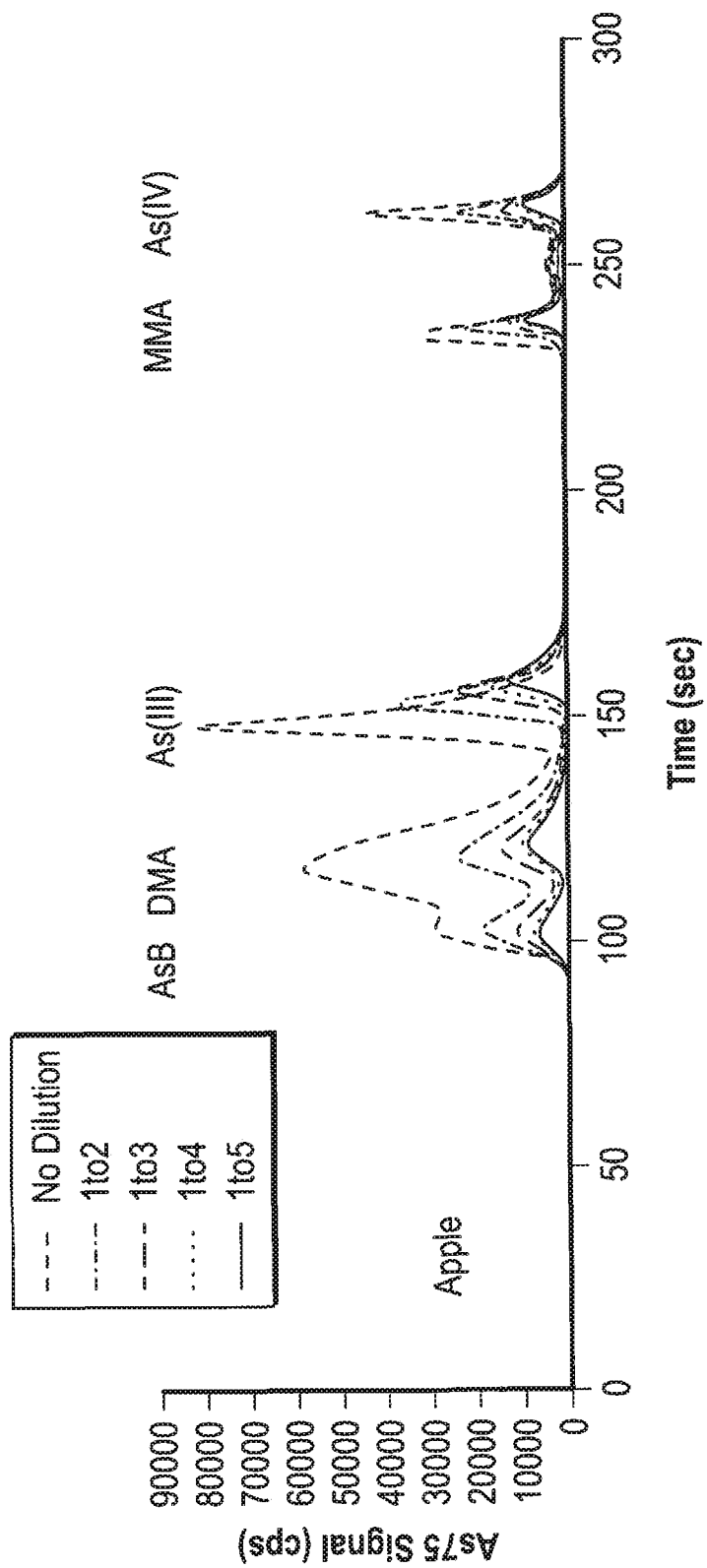
FIG. 4A is a chart showing detected arsenic over time for various dilutions of apple juice samples.
Figure 4B:
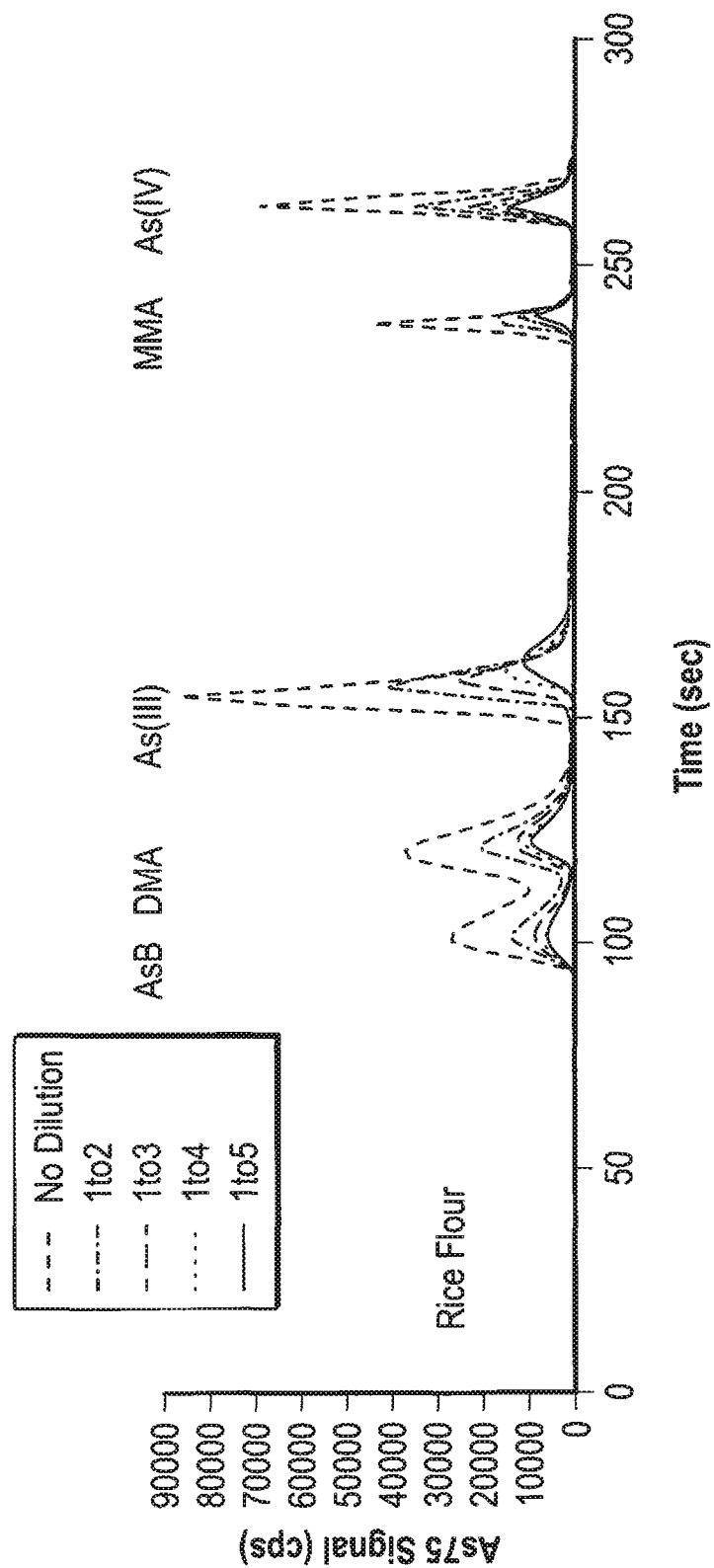
FIG. 4B is a chart showing detected arsenic over time for various dilutions of rice flour samples.

The dilution amount or ratio for inline dilution of a sample or standard (e.g. at the first valve 110, facilitated by the mixing portion) can depend on the species of interest to be analyzed. Referring to FIGS. 4A and 4B, charts are provided showing arsenic detected over time by an ICP spectrometry system (e.g., system 100 described herein) for various dilutions of apple juice samples (shown in FIG. 4A) and rice flour samples (shown in FIG. 4B). As shown, the effects of sample matrix on species elution are mitigated through sample dilution, where automated dilutions of 1 to 2, 1 to 3, 1 to 4, and 1 to 5 are provided. In implementations, for arsenic speciation, a five-fold dilution factor is utilized for separation of species of interest from apple juice and rice flour matrices.

In an example series of analyses, stable retention times were observed for eighteen (18) separate samples spanning over ten different matrices over ten days of speciation testing. The samples included apple juice, wine, soft drinks, iced tea, and rice flour extract. Table 2 provides data associated with the determined retention times.

TABLE 2

| | Retension Times (Seconds) | | | | |
|---|---|---|---|---|---|
| | Arsenobetaine | DMA | Arsenite | MMA | Arsenate |
| Average (All Samples) | 93 | 117 | 157 | 240 | 263 |
| Std. Deviation (All Samples) | 0.889 | 1.050 | 4.679 | 0.503 | 1.401 |
| % RSD (All Samples) | 1.0 | 0.9 | 3.0 | 0.2 | 0.5 |

Figure 6:
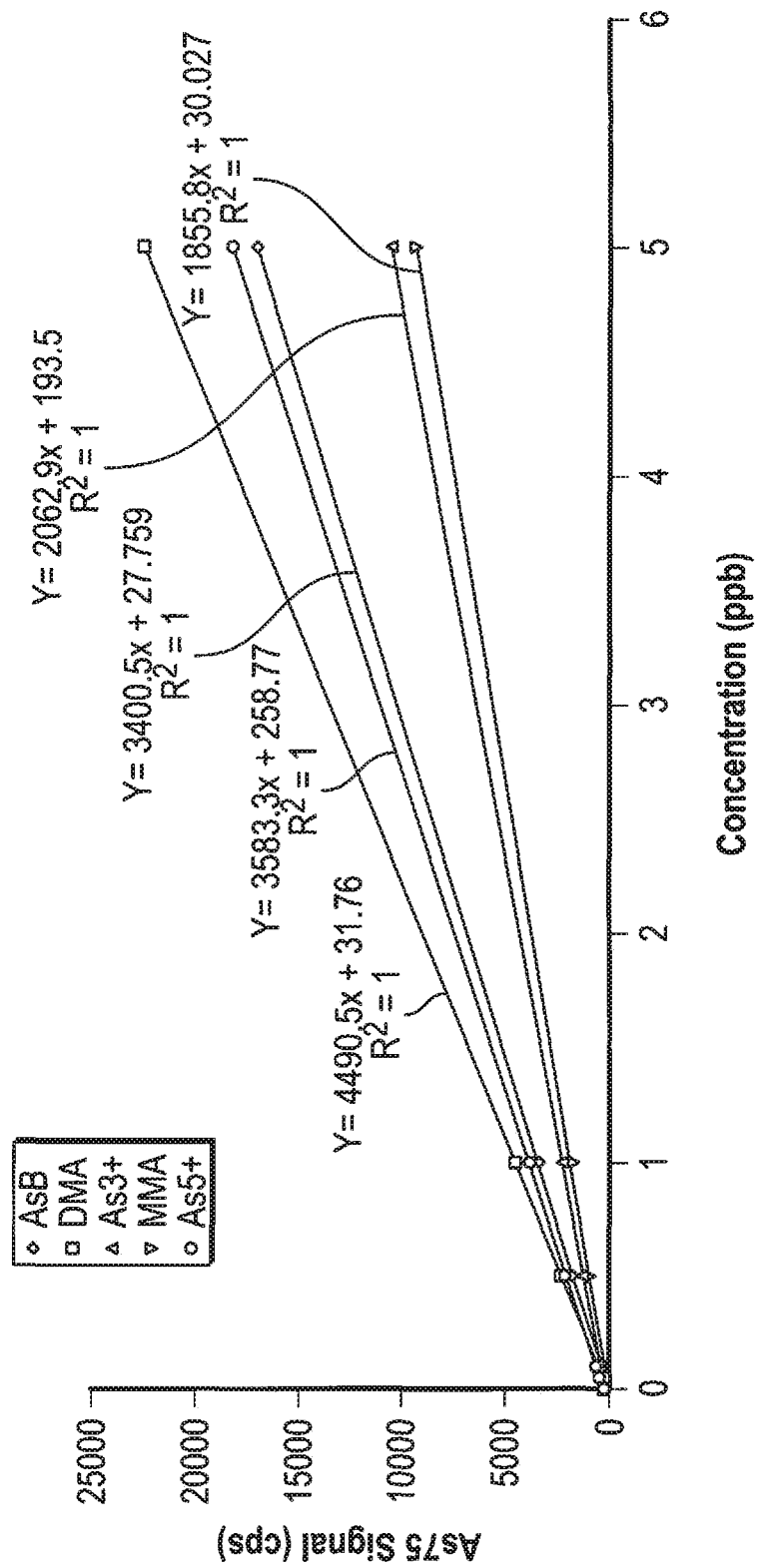
FIG. 6 is a chart for calibration curves for five of the major arsenic species resulting from auto-calibration.

In implementations, a calibration chromatogram can be generated by the system 100. For example, the system 100 can generate an auto-calibration of a single mixed standard (5 parts per billion (ppb) of each species) and a calibration blank. Referring to FIG. 5, a calibration chromatogram is shown via auto-calibration by system 100 of inline dilution of five arsenic species and a calibration blank. The dilutions include 50 parts per trillion (ppt), 100 ppt, 500 ppt, 1 ppb, and 5 ppb. The auto-calibration of inline dilution of the arsenic standard via system 100 resulted in highly linear calibration curves for all of the five major arsenic species, as shown in FIG. 6.

Example 1

Figure 7A:
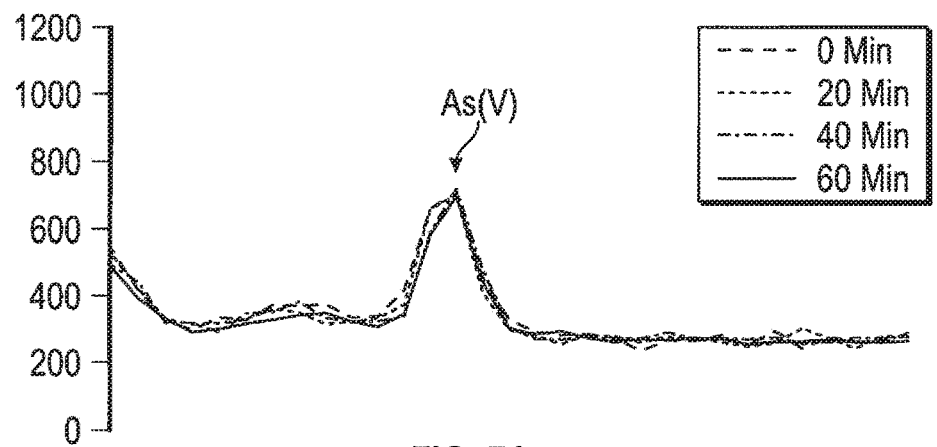
FIG. 7A is a chart showing an arsenic species detection over time for automated inline dilution.
Figure 7B:
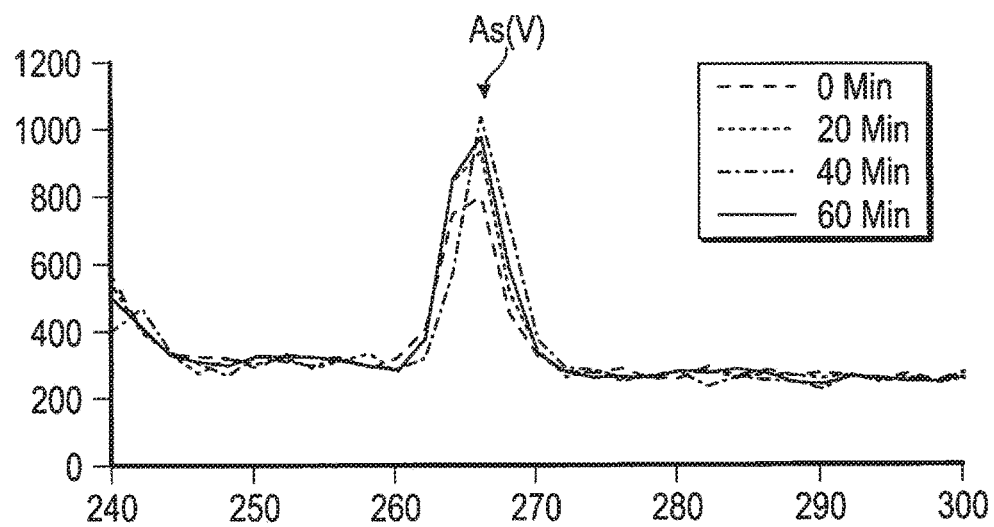
FIG. 7B is a chart showing an arsenic species detection over time for manual dilution with deionized water.
Figure 7C:
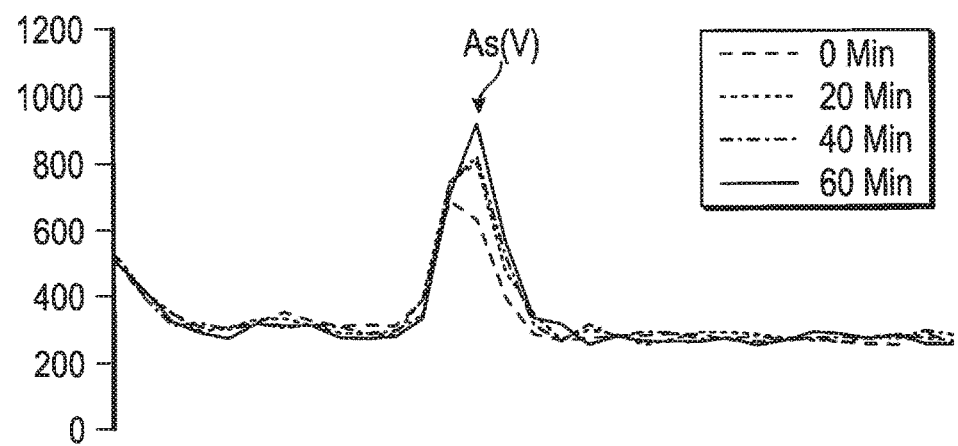
FIG. 7C is a chart showing an arsenic species detection over time for manual dilution with mobile phase.
Figure 8A:
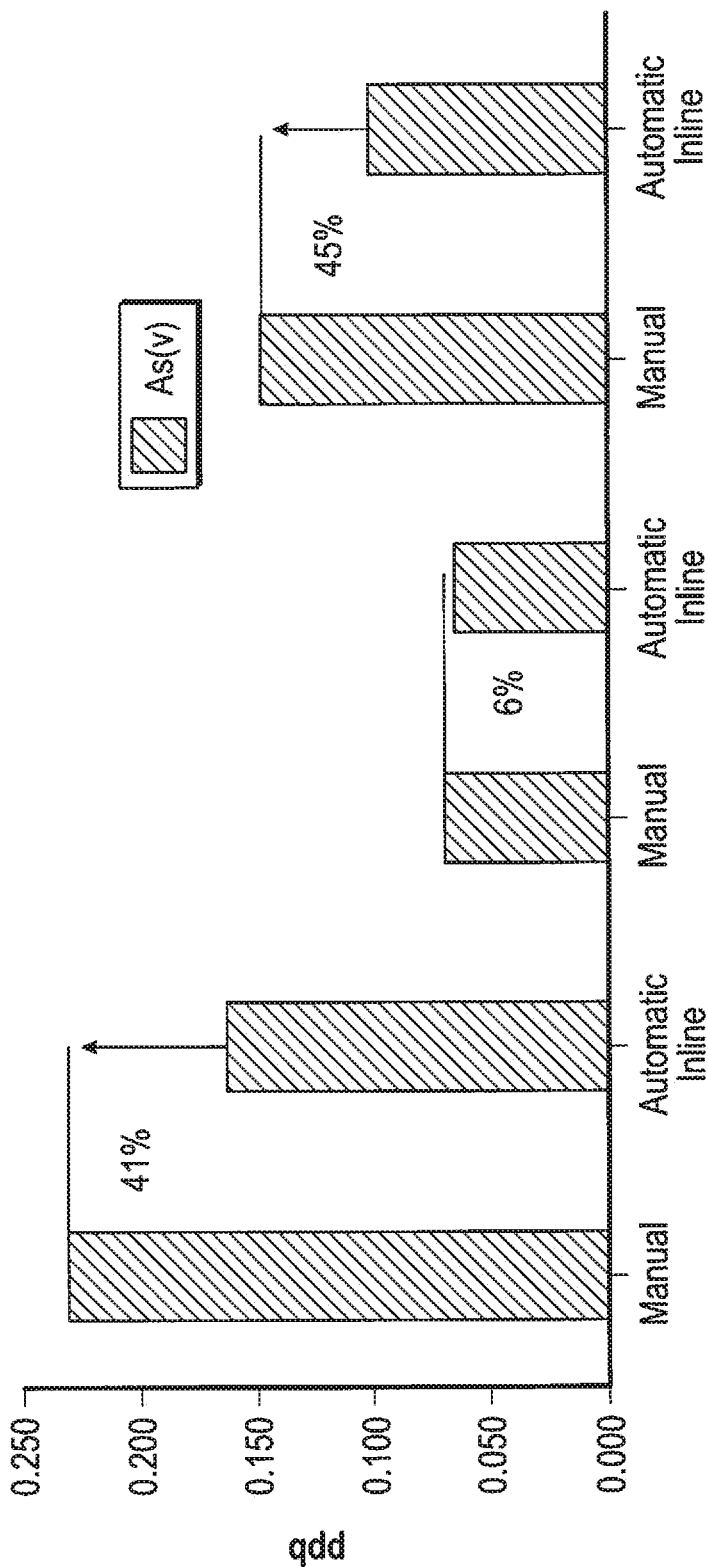
FIG. 8A is a chart illustrating effects of manual dilution on measured arsenate concentrations between various samples.
Figure 8B:
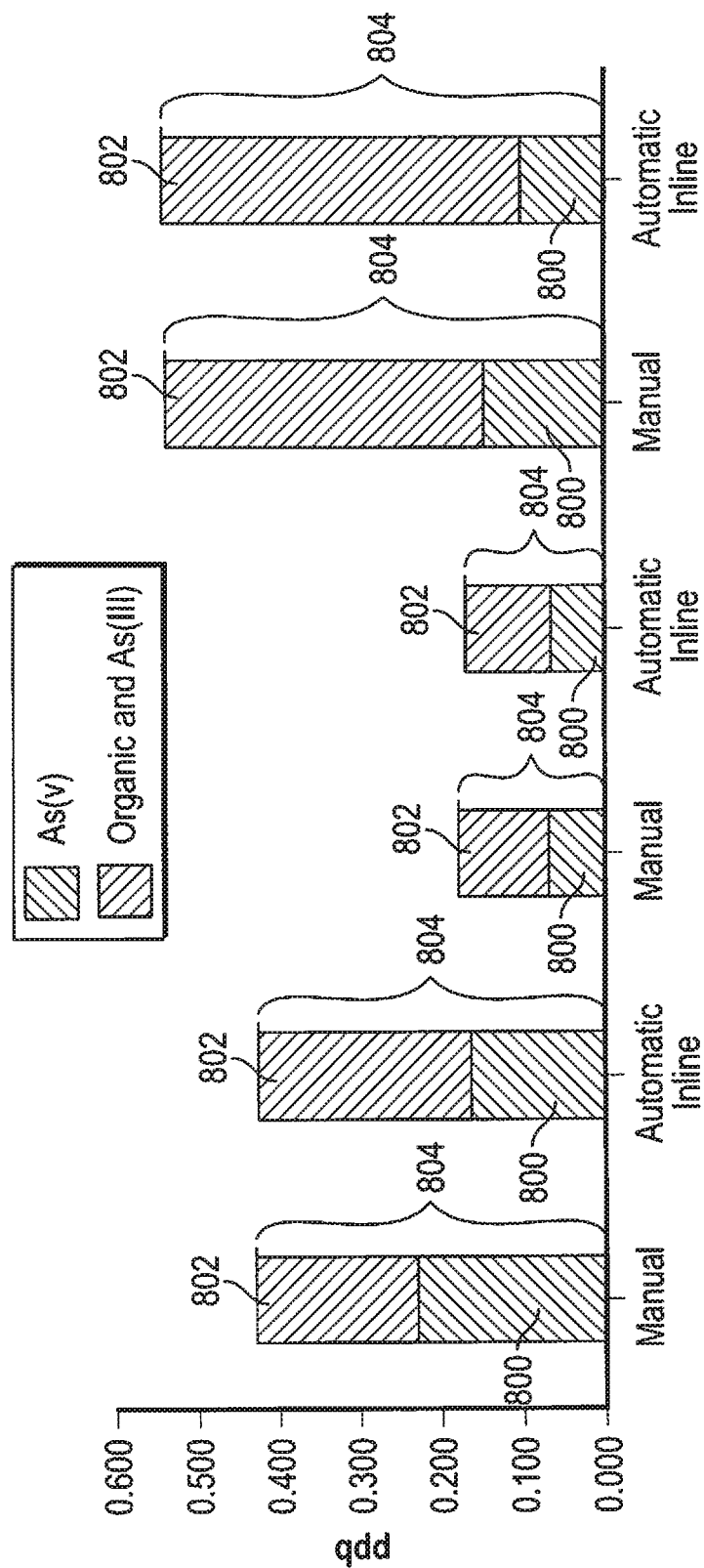
FIG. 8B is a chart illustrating effects of manual dilution on measured arsenic species concentrations between various samples.

Analyses of five-fold diluted apple juice were performed via ICP-MS, with three different dilution methods: automatic inline dilution with dilution at of sample at time t=zero minutes, twenty minutes, forty minutes, and sixty minutes, manual dilution with deionized water at time t=zero minutes, and manual dilution with mobile phase at time t=zero minutes. The results of arsenate (As(V)) detection for the automatic inline dilution method is shown in FIG. 7A; the results of arsenate (As(V)) detection for the manual dilution with deionized water is shown in FIG. 7B; and the results of arsenate (As(V)) detection for the manual dilution with mobile phase is shown in FIG. 7C. As shown, the detected amounts of arsenate remained consistent over the sixty minute analysis for the automatic inline dilution (e.g., FIG. 7A), whereas the detected amounts of arsenate for each of the manual dilutions (e.g., FIGS. 7B and 7C) increased over time. Referring to FIGS. 8A and 8B, the effects of manual dilution on three different apple juice concentrations can be seen. FIG. 8A shows the detected concentrations of arsenate (As(V)) for each of the three apple juice samples for manual dilution (where all samples are diluted at time t=zero) and for automated inline dilution (where samples are diluted at time t=zero minutes, twenty minutes, forty minutes, and sixty minutes), including the percent difference in the detected values. As can be seen, the percent difference between the manual and automated inline dilution methods includes a forty-one percent difference, a six percent difference, and a forty-five percent difference, where in all instances, the manual dilution samples exhibited a higher detection of arsenate than the automatic inline dilution samples. The total amount of measured arsenic (organic and inorganic species) is shown in FIG. 8B, as well as the detected amounts of arsenate (labeled 800) and the detected amounts of organic species and arsenite (As(III)) (labeled 802). As can be seen, the total amount of arsenic (labeled 804) measured remains the same between the manual dilution samples and the automatic inline samples, however the breakdown between the amounts of the detected species differs (e.g., 800 differs between manual dilution and automatic dilution samples; 802 differs between manual dilution and automatic dilution samples). In particular, the manual dilution samples all exhibit a higher detection of arsenate 800 than the automatic inline dilution samples (as also shown in FIG. 8A) and a lower detection of the remainder of arsenic species 802 (i.e., the organic and arsenite species). While not being bound to any specific chemical conversion pathways, the organic species of arsenic could convert to arsenate when diluted and permitted to remain untested for a period of time (e.g., for up to sixty minutes in the example tests provided herein above), thereby rendering an inaccurate analysis of the amounts of arsenic species present in the various samples. The automatic inline dilution provides nearly instantaneous dilution and sampling, so no substantial time is provided for the conversion of the arsenic species.

Figure 9:
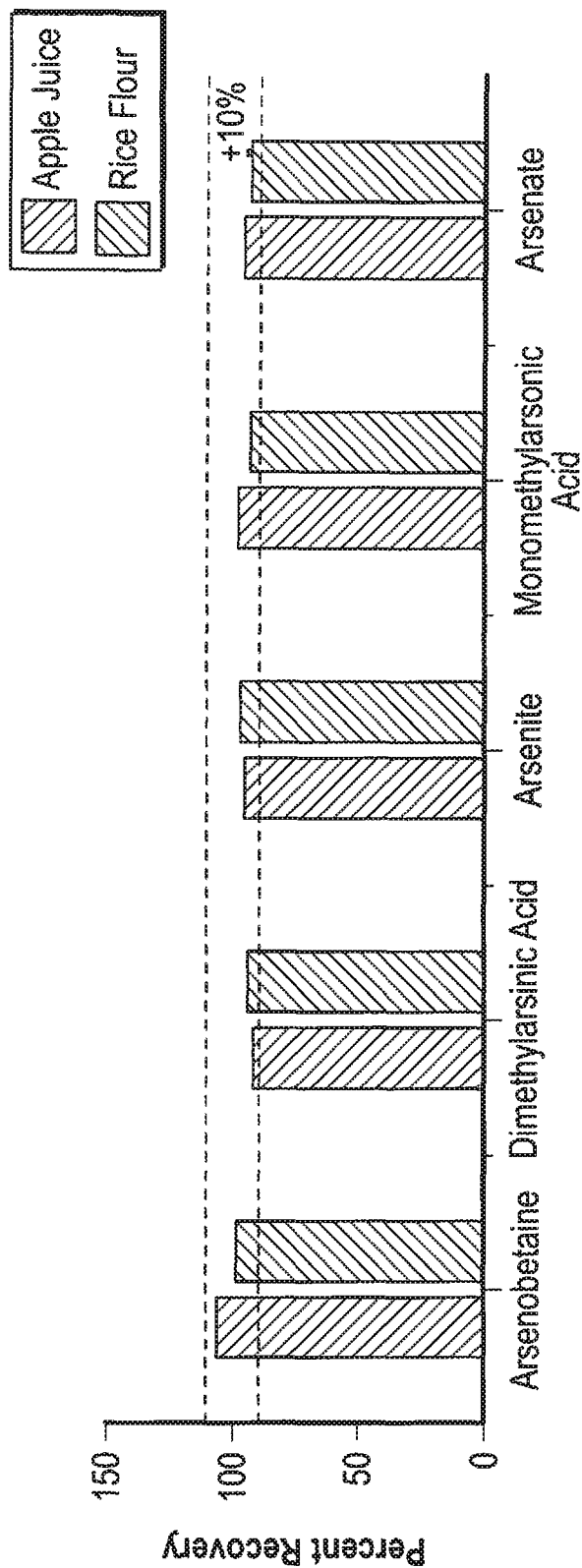
FIG. 9 is a chart illustrating spike recovery for five of the major arsenic species for apple juice and rice flour extraction matrices.

Referring to FIG. 9, a percent recovery of each of five major arsenic species provided during automatic inline dilution of apple juice and rice flour samples is shown, where all recoveries are within a (plus or minus) ten percent margin for both apple juice and rice flour extraction matrices.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:
1. A system comprising:
a first valve, the first valve having a first valve configuration to receive a sample fluid from a sampling device into a holding loop coupled to the first valve;
a plurality of syringe pumps coupled to the first valve, the plurality of syringe pumps including a carrier syringe pump configured to supply a carrier fluid to the first valve in a second valve configuration, a diluent syringe pump configured to supply a diluent fluid to the first valve in the second valve configuration, and a standard syringe pump configured to supply a standard fluid to the first valve in the second valve configuration, the first valve configured to mix at least two of the diluent fluid, the standard fluid, or the sample fluid to form an inline diluted sample, the first valve configured to deliver the inline diluted sample therefrom; and
a second valve coupled to the first valve, the second valve having a first valve configuration configured to receive the inline diluted sample from the first valve into a sample holding loop coupled to the second valve, the second valve configured to couple to at least one of an eluent source or a carrier fluid source and having a second valve configuration to receive at least one of an eluent fluid from the eluent source or a carrier fluid from the carrier fluid source to transfer the inline diluted sample from the sample holding loop to a speciation column to separate one or more species from the inline diluted sample from respective other species of the inline diluted sample.

2. The system of claim 1, further comprising a computer system operably coupled to the diluent syringe pump and the standard syringe pump.

3. The system of claim 2, wherein the computer system is configured to control a flow rate output by each of the diluent syringe pump and the standard syringe pump according to an inline dilution factor.

4. The system of claim 3, wherein the inline dilution factor is stored on a non-transitory carrier medium accessible by the computer system.

5. The system of claim 3, wherein the computer system is configured to control the flow rate output by each of the diluent syringe pump and the standard syringe pump according to a plurality of inline dilution factors.

6. The system of claim 5, wherein the computer system is configured to generate a calibration curve based on analysis by an inductively coupled plasma spectrometry system of the inline diluted sample according to the plurality of inline dilution factors.

7. The system of claim 1, wherein the speciation column is coupled to an inductively coupled plasma torch assembly.

8. The system of claim 7, wherein the speciation column is coupled to an injector of the inductively coupled plasma torch assembly.

9. The system of claim 1, further comprising a speciation bypass valve coupled between the second valve and the speciation column.

10. The system of claim 9, wherein the speciation bypass valve includes a speciation configuration to provide a first flow path from the second valve to the speciation column to an inductively coupled plasma torch assembly, and wherein the speciation bypass valve includes a speciation bypass configuration to provide a second flow path from the second valve to the inductively coupled plasma torch assembly bypassing the speciation column.

* * * * *